US009151740B2

(12) United States Patent  
Lee et al.

(10) Patent No.: US 9,151,740 B2  
(45) Date of Patent: Oct. 6, 2015

(54) NANOPORE DEVICE WITH IMPROVED SENSITIVITY AND METHOD OF FABRICATING THE SAME

(75) Inventors: Jong-ho Lee, Seoul (KR); Jun-mo Park, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 214 days.

(21) Appl. No.: 13/614,570

(22) Filed: Sep. 13, 2012

(65) Prior Publication Data

US 2013/0240378 A1     Sep. 19, 2013

(30) Foreign Application Priority Data

Mar. 13, 2012   (KR) .................. 10-2012-0025664

(51) Int. Cl.
| | |
|---|---|
| *G01N 27/26* | (2006.01) |
| *G01N 33/487* | (2006.01) |
| *B82Y 5/00* | (2011.01) |
| *B82Y 40/00* | (2011.01) |
| *B82Y 15/00* | (2011.01) |

(52) U.S. Cl.
CPC ............. *G01N 33/48721* (2013.01); *B82Y 5/00* (2013.01); *B82Y 15/00* (2013.01); *B82Y 40/00* (2013.01)

(58) Field of Classification Search
CPC ....... G01N 33/48721; G01N 27/414–27/4148; G01N 33/54373; G01N 27/3278; B82Y 15/00; B82Y 40/00; B82Y 5/00; C12Q 2565/631; Y10S 977/852; Y10S 977/733; Y10S 977/72; Y10S 977/721
See application file for complete search history.

(56) References Cited

U.S. PATENT DOCUMENTS

| | | | |
|---|---|---|---|
| 6,846,702 B1 | 1/2005 | Barth | |
| 2010/0327255 A1 | 12/2010 | Peng et al. | |
| 2012/0171778 A1* | 7/2012 | Yang et al. ..................... | 436/501 |
| 2013/0240359 A1* | 9/2013 | Turner et al. .................. | 204/451 |

FOREIGN PATENT DOCUMENTS

| | | |
|---|---|---|
| KR | 10-0730350 B1 | 6/2007 |
| KR | 10-2011001896 A | 6/2011 |

OTHER PUBLICATIONS

Kim et al., *Biosensors and Bioelectronics*, "Nanopore Sensor for Fast Label-Free Detection of Short Double-Stranded DNAs," 22: 2926-2931 (2007).

Musso, Michael., web page printout downloaded from <<http://genecuisine.blogspot.com/2011/03/nanopore-sequencing.html>>on Nov. 24, 2014.

* cited by examiner

*Primary Examiner* — Gurpreet Kaur
(74) *Attorney, Agent, or Firm* — Leydig, Voit & Mayer, Ltd.

(57) ABSTRACT

A nanopore device comprising a channel unit comprising a micro channel defined by a bottom surface and an insulator lateral wall; and a cover unit covering the micro channel, wherein the cover unit comprises a nanopore extending through the cover unit and connected to the micro channel; a first source/drain electrode disposed on an upper surface of the cover unit and adjacent to an inlet of the nanopore; an opening extending through the cover unit and connected to the micro channel; and a second source/drain electrode disposed on the upper surface of the cover unit and adjacent to the opening; as well as a method for fabricating and using the device.

17 Claims, 21 Drawing Sheets

NANOPORE DEVICE WITH IMPROVED SENSITIVITY AND METHOD OF FABRICATING THE SAME

CROSS-REFERENCE TO RELATED APPLICATIONS

This application claims the benefit of Korean Patent Application No. 10-2012-0025664, filed on Mar. 13, 2012, in the Korean Intellectual Property Office, the disclosure of which is incorporated herein in their entirety by reference.

BACKGROUND

A variety of methods for detecting target biomolecules such as deoxyribonucleic acid (DNA) and DNA sequencing in a sample have been developed. Among these methods, a nanopore method has been used in conjunction with a DNA detection system with high sensitivity. A nanopore DNA detection system detects DNA from a slight change in electric current which occurs when DNA translocates through nanopores to perform DNA sequencing or to determine whether double-stranded or single-stranded DNA is present.

For example, a DNA detection system includes a nanopore formed through a thin film including an insulating layer/conductive gate layer/insulating layer, upper and lower sample solution reservoirs that are formed in such a manner that the nanopore is disposed therebetween, and source and drain electrodes that are respectively put in the upper and lower sample solution reservoirs. A sample solution of an electrolyte such as KCL including target biomolecules such as DNA may be filled in the upper and lower sample solution reservoirs and the nanopore.

In this structure, when a bias is applied to the conductive gate layer, target biomolecules exhibiting an electric charge in the sample solution of an electrolyte may translocate through the nanopore. In this case, target biomolecules translocating through the nanopore may be identified or DNA sequencing may be performed by measuring an electric current between the source and drain electrodes and measuring a turn-on gate voltage applied to the conductive gate layer.

There is a need to perform more accurate measurements by increasing the sensitivity of conventional nanopore DNA detection systems. There is also a need to increase measuring speed of conventional nanopore DNA detection systems.

SUMMARY

Provided is a nanopore device that increases sensitivity by reducing a diameter of a nanopore or a thickness of a conductive gate layer, and a method of fabricating the same.

Provided is a nanopore device by which an array including a plurality of nanopores may be easily configured and in which a signal amplifying circuit is installed together, and a method of fabricating the nanopore device.

Additional aspects will be set forth in part in the description which follows and, in part, will be apparent from the description, or may be learned by practice of the presented embodiments.

According to an aspect of the present invention, a nanopore device includes a channel unit including a micro channel defined by a bottom surface and an insulator lateral wall; and a cover unit covering an upper portion of the micro channel, wherein the cover unit includes a nanopore that is extending through the cover unit and connected to the micro channel; a first source/drain electrode that is formed on an upper surface of the cover unit and adjacent to an inlet of the nanopore; an opening extending through the cover unit and connected to the micro channel; and a second source/drain electrode that is formed on the upper surface of the cover unit so as to be adjacent to the opening.

In some embodiments, the cover unit may further include a gate electrode disposed in the cover unit and surrounding the nanopore.

In some embodiments, the cover unit may further include a gate insulating layer that covers the gate electrode on an internal wall of the nanopore.

In some embodiments, the nanopore device may further include a gate contact plug extedning through the cover unit and electrically connected to the gate electrode; and a contact unit disposed on an upper surface of the cover unit and electrically connected to the gate contact plug, the first source/drain electrode, and the second source/drain electrode through electrical wirings, respectively.

In some embodiments, the gate electrode may have a thickness of about 0.3 nm to about 0.4 nm, and the nanopore may have an internal diameter of about 1 nm to about 1.5 nm at a portion where the gate electrode is disposed.

In some embodiments, the cover unit may further include a first solution reservoir that protrudes from the upper surface of the cover unit so as to surround the nanopore and the first source/drain electrode; and a second solution reservoir that protrudes from the upper surface of the cover unit so as to surround the opening and the second source/drain electrode.

In some embodiments, the first solution reservoir and second solution reservoir may comprise a surface that is hydrophobic. For example, the first solution reservoir and the second solution reservoir may each be formed with a hydrophobic wall.

In some embodiments, the cover unit may include a plurality of first solution reservoirs.

In some embodiments, the cover unit may include a plurality of nanopores and a plurality of first source/drain electrodes that are respectively disposed in the plurality of first solution reservoirs.

In some embodiments, the second solution reservoir may be disposed between the plurality of first solution reservoirs.

In some embodiments, the bottom surface of the microchannel may be formed of a semiconductor material.

In some embodiments, the nanopore device may further include at least one column in the microchannel that is connected to the bottom surface of the microchannel and a lower (bottom) surface of the cover unit (i.e., extending between the cover unit and the bottom surface of the microchannel) wherein the at least one column supports the cover unit, at least in part.

In some embodiments, the cover unit may be formed by stacking at least one insulating layer. For example, the cover unit may include a first insulating layer, a second insulating layer formed on the first insulating layer, a third insulating layer formed on the second insulating layer, and a fourth insulating layer formed on the third insulating layer. In this case, the third insulating layer may be formed of a different material from that of the second insulating layer and the third insulating layer.

In some embodiments, the cover unit may include a gate electrode that is disposed between the first insulating layer and the second insulating layer so as to surround the nanopore.

In some embodiments, the first source/drain electrode may have a ring shape so as to surround the inlet of the nanopore.

In some embodiments, to opening area of the opening may be greater than an opening area of the nanopore.

According to another aspect of the present invention, a method of fabricating a nanopore device includes sequentially stacking first, second, and third insulating layers on a semiconductor substrate including an active region and an insulator lateral wall surrounding the active region; forming an opening and a plurality of first via holes through the first through third insulating layers so as to expose the active region; forming a micro channel by etching a portion of the active region, which is below the first insulating layer, through the opening and the plurality of first via holes; stacking a fourth insulating layer on the third insulating layer; forming a nanopore through the first through fourth insulating layers so as to be connected to the micro channel; and forming a first source/drain electrode adjacent to an inlet of the nanopore and a second source/drain electrode adjacent to the opening on the fourth insulating layer.

For example, a semiconductor substrate including the active region and the insulator lateral wall may be formed by using a shallow trench isolation (STI) process.

In some embodiments, the sequential stacking of first through third insulating layers may include forming the first insulating layer on the semiconductor substrate; partially forming a gate electrode on the first insulating layer; forming a second insulating layer on the first insulating layer on which the gate electrode is formed; forming the third insulating layer having a different etch rate from the second insulating layer on the second insulating layer; forming a second via hole through the third insulating layer so as to face the gate electrode; etching the second insulating layer so as to expose the gate electrode through the second via hole; and filling a spacer in a space obtained by removing the second insulating layer.

In some embodiments, the gate electrode may be formed over an interface between the active region and the insulator lateral wall.

In some embodiments, the thickness of the gate electrode may be about 0.3 nm to about 0.4 nm.

In some embodiments, the first, second, and fourth insulating layers may be formed of silicon oxide, and the third insulating layer may be formed of silicon nitride.

In some embodiments, the spacer may be formed of the same material as the second insulating layer.

In some embodiments, the etching of the second insulating layer may use, for example, wet etching.

In some embodiments, the plurality of first via holes may be arranged along columns and rows at a regular interval, and a barrier having a horizontal cross-sectional area that is greater than a size of each first via hole may be formed between the plurality of first via holes.

In some embodiments, the forming of the micro channel may include wet-etching the active region in an under-cut manner so as to form at least one column below the barrier disposed between the plurality of first via holes.

In some embodiments, the forming of the nanopore may include forming a mask layer on the fourth insulating layer and forming a mask pattern by etching the mask layer so as to remove a portion of the mask layer corresponding to the second via hole; exposing the second via hole by etching the fourth insulating layer through the mask pattern; forming a nanopore by sequentially etching the spacer, the gate electrode, and the first insulating layer through the mask pattern and the second via hole; and removing the mask layer.

In some embodiments, the method may further include forming a gate insulating layer so as to cover at least the gate electrode on an internal wall of the nanopore.

In some embodiments, the gate insulating layer may be formed by using, for example, a thermal oxidation process.

In some embodiments, the internal diameter of the nanopore, which is reduced by the gate insulating layer, may be about 1 nm to about 1.5 nm at a portion where the gate electrode is disposed.

In some embodiments, the method may further include forming a gate contact plug that is electrically connected to the gate electrode by sequentially etching the fourth insulating layer, the third insulating layer, and the second insulating layer.

Also provided is a method of analyzing a nucleic acid molecule comprising contacting the nanopore of the nanopore device with a sample comprising a nucleic acid (e.g., RNA or DNA), applying an electic current between the first and second source/drain electrodes, and detecting a change in the voltage between the first and second source/drain electrodes, or detecting a change in the voltage at the gate electrode. The relative magnitude of a change in the voltage between the first and second source/drain electrodes indicates the relative size of a base of the nucleic acid passing through the nanopore.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
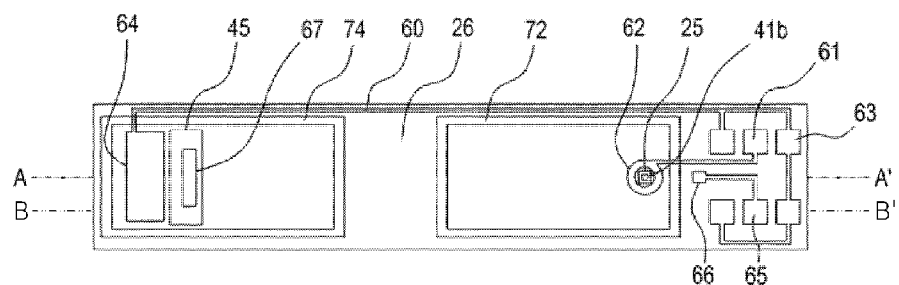
FIG. 1 is a plan view of a nanopore device according to an embodiment of the present invention.

Hereinafter, reference will now be made in detail to embodiments of a nanopore device, and a method of fabricating the same, examples of which are illustrated in the accompanying drawings, wherein like reference numerals refer to like elements throughout. In this regard, lengths and sizes of layers and regions may be exaggerated for clarity. As used herein, the term "and/or" includes any and all combinations of one or more of the associated listed items.

Figure 2A:
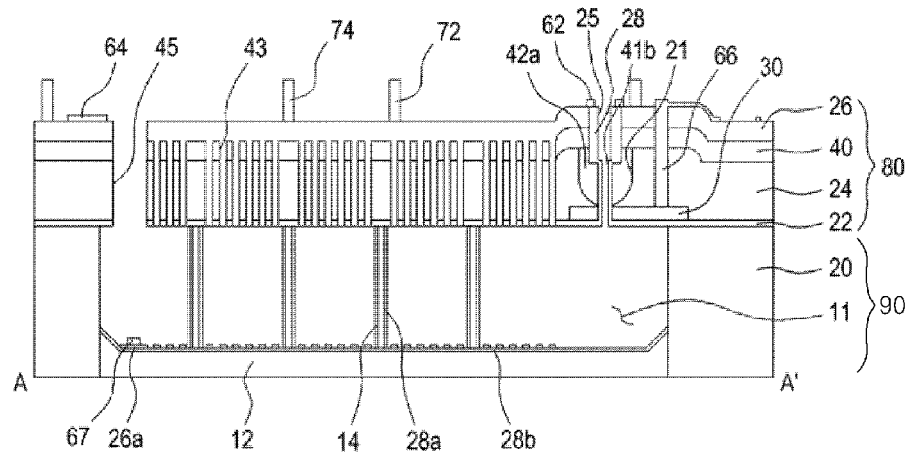
FIG. 2A is a cross-sectional view of the nanopore device taken along a line A-A' of FIG. 1, according to an embodiment of the present invention.
Figure 2B:
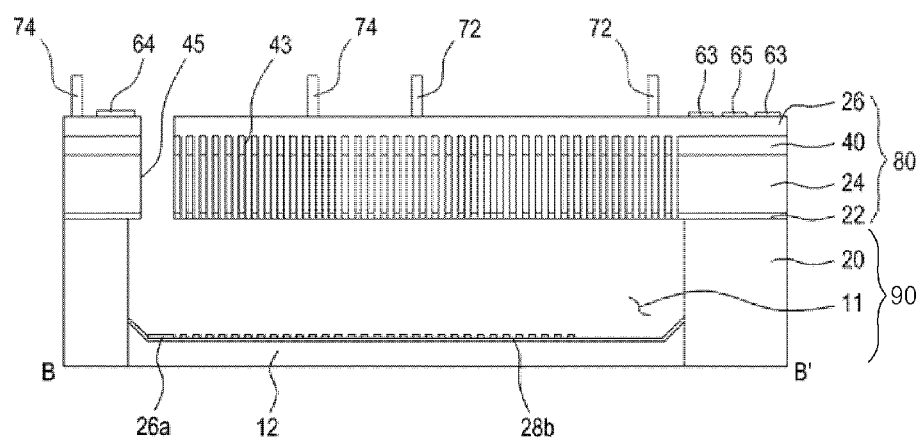
FIG. 2B is a cross-sectional view of the nanopore device taken along a line B-B' of FIG. 1, according to an embodiment of the present invention.

FIG. 1 is a plan view of a nanopore device according to an embodiment of the present invention. FIG. 2A is a cross-sectional view of the nanopore device taken along a line A-A' of FIG. 1, according to an embodiment of the present invention. FIG. 2B is a cross-sectional view of the nanopore device taken along a line B-B' of FIG. 1, according to an embodiment of the present invention.

Referring to FIGS. 1, 2A, and 2B, the nanopore device according to the present embodiment may include a channel unit 90 including a micro channel 11 that is surrounded and defined by a bottom surface 12 and an insulator lateral wall 20 surrounding a perimeter of the micro channel 11. The insulator lateral wall 20 joins the bottom surface 12 along a lower periphery of the micro channel 11. The micro channel 11 has a space with a predetermined length and width, and an insulator cover unit 80 covering an upper portion of the micro channel 11. The cover unit may contact with and join the insulator lateral wall 20 along an upper periphery of the micro channel 11. The cover unit 80 may include a nanopore 41b that is perpendicularly formed through the cover unit 80 and is connected to one end of the micro channel 11, a gate electrode 30 formed in the cover unit 80 to surround the nanopore 41b, a first source/drain electrode 62 that is formed on an upper surface of the cover unit 80 so as to be adjacent to an inlet 25 of the nanopore 41b, an opening 45 that is perpendicularly formed through the cover unit 80 and is connected to the other end of the micro channel 11, and a second source/drain electrode 64 that is formed on the upper surface of the cover unit 80 so as to be adjacent to the opening 45. The cover unit 80 may further include a first solution reservoir 72 that is formed on the upper surface of the cover unit 80 so as to surround the nanopore 41b and the first source/drain electrode 62, and a second solution reservoir 74 that protrudes on the upper surface of the cover unit 80 so as to surround the opening 45 and the second source/drain electrode 64. When in use, an electrolyte solution (not shown) including a target material, for example, deoxyribonucleic acid (DNA), may be filled in and occupy the first solution reservoir 72, the second solution reservoir 74, the nanopore 41b, the opening 45, and/or the micro channel 11.

The bottom surface 12 of the micro channel 11 may be formed of an insulating material, or may be formed of a semiconductor material such as silicon. When the bottom surface 12 is formed of a semiconductor material, the nanopore device may be easily formed by using a general semiconductor processing method. For example, the insulator lateral wall 20 may be provided by an insulator material disposed on a semiconductor substrate, for instance, by forming an insulating layer around the periphery of a semiconductor substrate by using a general shallow trench isolation (STI) process. The cover unit 80 and the micro channel 11 may be formed by providing additional insulator layers and etching a central portion of the semiconductor substrate. A method of fabricating the nanopore device will be described below in more detail.

Referring to FIG. 2A, the nanopore device according to the present embodiment may further include at least one column, that is, columns 14 and 28a that support the cover unit 80 in the micro channel 11. The columns 14 and 28a may be connected between an upper surface of the bottom surface 12 and a lower surface of the cover unit 80 and may support the cover unit 80 and the first and second solution reservoirs 72 and 74 disposed on the upper surface of the cover unit 80. The columns 14 and 28a may be arranged at a regular interval, or may be irregularly arranged. The arrangement of columns may be selected so that target materials may easily translocate through the micro channel 11.

The cover unit 80 may be formed by sequentially stacking at least one insulating layer, for example, four insulating layers 22, 24, 26, and 40. For example, the insulating layers 22, 24, 26, and 40 may include oxide insulating layers 22, 24, and 26, and a nitride insulating layer 40. By forming the cover unit 80 by using the insulating layers 22, 24, 26, and 40, the nanopore 41b may be formed as small as possible in consideration of the size of an object (e.g., a single-stranded DNA) to be identified, the micro channel 11 may be formed in the channel unit 90, and the gate electrode 30 may be disposed in the cover unit 80. That is, the insulating layers 22, 24, 26, and 40 may be chosen in consideration of a manufacturing process. Alternatively, a single insulating layer may constitute the cover unit 80.

The first source/drain electrode 62 that is formed on the upper surface of the cover unit 80 so as to be adjacent to the inlet 25 of the nanopore 41b may have, for example, a ring shape so as to surround the inlet 25 of the nanopore 41b. In general, when a single-stranded DNA is analyzed, a negative voltage having the same polarity as DNA is applied to the first source/drain electrode 62 and a positive voltage is applied to the second source/drain electrode 64. Thus, when the first source/drain electrode 62 having a ring shape symmetrically surrounds the inlet 25 of the nanopore 41b, an electrical repulsive force generated by the first source/drain electrode 62 may symmetrically act on bases of DNA translocating through the nanopore 41b, thereby reducing sensing signal noise that is measured through the gate electrode 30.

The opening 45 may guide target materials, which translocate to the micro channel 11 through the nanopore 41b, to the second solution container 74. Thus, the opening 45 does not have to be minutely formed like the nanopore 41b, and a diameter of the opening 45 may be greater than a diameter of the nanopore 41b. For example, a diameter of the nanopore 41b may be about 1 nm to about 1.5 nm and a diameter of the opening 45 may be several mm.

The first and second solution reservoirs 72 and 74 for containing an electrolyte solution including target materials may be formed on the upper surface of the cover unit 80 to each have a barrier rib or wall. In this case, a surface of the wall of each of the first and second solution reservoirs 72 and 74 may be processed to be hydrophobic so that target materials may not be attached thereto. For example, the first and second solution reservoirs 72 and 74 may comprise or be formed of a photosensitive film or polydimethysiloxane (PDMS). However, the materials and shapes of the first and second solution reservoirs 72 and 74 are not particularly limited as long as the first and second solution reservoirs 72 and 74 may contain an electrolyte solution.

The cover unit 80 may further include a gate insulating layer 28 that is formed to cover the gate electrode 30 on an internal wall of the nanopore 41b. When the gate insulating layer 28 covering the gate electrode 30 is formed on the internal wall of the nanopore 41b, the nanopore device according to the present embodiment may operate as an ionic field effect transistor (IFET). In addition, a gate contact plug 66 that is perpendicularly formed through the cover unit 80 so as to be electrically connected to the gate electrode 30 may be further formed on the cover unit 80. One end of the gate contact plug 66 may contact the gate electrode 30 and the other end of the gate contact plug 66 may be exposed through the upper surface of the cover unit 80. However, the nanopore device does not have to operate as a transistor. For example, the nanopore device may operate by using only the first source/drain electrode 62 and the second source/drain electrode 64 without the gate electrode 30.

Contact units 65, 61, and 63 may be further formed on the upper surface of the cover unit 80 so as to be electrically connected to the gate contact plug 66, the first source/drain electrode 62, and the second source/drain electrode 64 through wirings 60, respectively. Although not illustrated, signal amplifying circuits that are respectively connected to the gate contact plug 66, the first source/drain electrode 62, and the second source/drain electrode 64 so as to amplify measuring signals may be further formed on the upper surface of the cover unit 80.

The gate electrode 30 having conductivity may be formed of metal but also may be formed of, for example, a silicon-based material (e.g., polycrystalline silicon) doped with impurities. Since an interval between bases of DNA is about 0.33 nm and a diameter of a single-stranded DNA is about 1 nm, a thickness of the gate electrode 30 may be about 0.3 nm to about 0.4 nm and an internal diameter of the nanopore 41b may be about 1 nm to about 1.5 nm at a portion where the gate electrode 30 is disposed. The thickness of the gate electrode 30 and the diameter of the nanopore 41b may be restricted (small), thereby preventing two or more bases from translocating through the gate electrode 30 simultaneously, and preventing two or more single-stranded DNA from translocating through the nanopore 41 b simultaneously. Accordingly, the nanopore device according to the present embodiment may increase measurement sensitivity for analyzing a base sequence of a single-stranded DNA.

In the above-described nanopore device according to the present embodiment, an electrolyte solution, for example, KCl may be filled in and occupy the first solution reservoir 72, the second solution reservoir 74, the nanopore 41b, the opening 45, and the micro channel 11 and a sample containing a target material such as DNA may be further added in the first solution reservoir 72. Then, when a negative voltage is applied to the first source/drain electrode 62, a positive voltage is applied to the second source/drain electrode 64, and when a bias is applied to the gate electrode 30, the nanopore 41b enters a turn-on state. In this case, a target material having negative polarity such as DNA may translocate from the first solution reservoir 72 to the micro channel 11 through the nanopore 41b. While the target material is translocating through the nanopore 41b, a voltage of the gate electrode 30 is changed or a current flowing between the first source/drain electrode 62 and the second source/drain electrode 64 is changed according to the size of a base, and thus, a base sequence may be determined by measuring the change in the voltage or the current.

Figure 3:
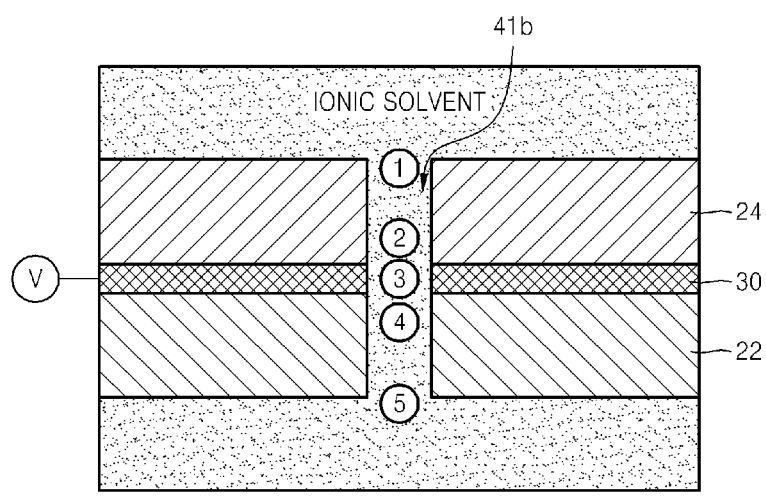
FIG. 3 is a simulation diagram showing a base sequence of single-stranded deoxyribonucleic acid (DNA) being analyzed by using a nanopore device, according to an embodiment of the present invention.

FIG. 3 is a simulation diagram showing a base sequence of single-stranded DNA being analyzed by using a nanopore device, according to an embodiment of the present invention. In FIG. 3, for convenience of description, only the insulating layers 22 and 24 around the gate electrode 30 and the nanopore 41b are schematically shown. In addition, in FIG. 3, bases that are positioned at five different positions in the nanopore 41b are shown for the purposes of illustration.

Figure 4:
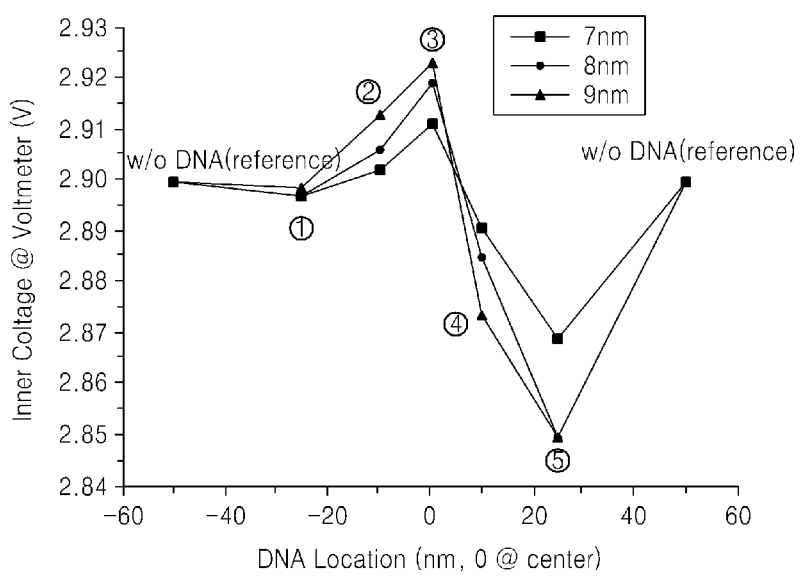
FIG. 4 is a graph showing characteristics whereby a voltage of a gate electrode is changed according to the size of a base and a position through which a base translocates when bases having different sizes translocate through a nanopore.

FIG. 4 is a graph showing changes in the voltage measured at the gate electrode is changed as a nucleic acid translocates through a nanopore. The change in voltage reflects the size of a base and its position in the nanopore. In FIG. 4, ① through ⑤ corresponds to positions of the bases shown in FIG. 3. Referring to FIG. 4, as the size of a base is increased, a voltage of the gate electrode 30 is changed more when the base translocates through the nanopore 41b.

Figure 5:
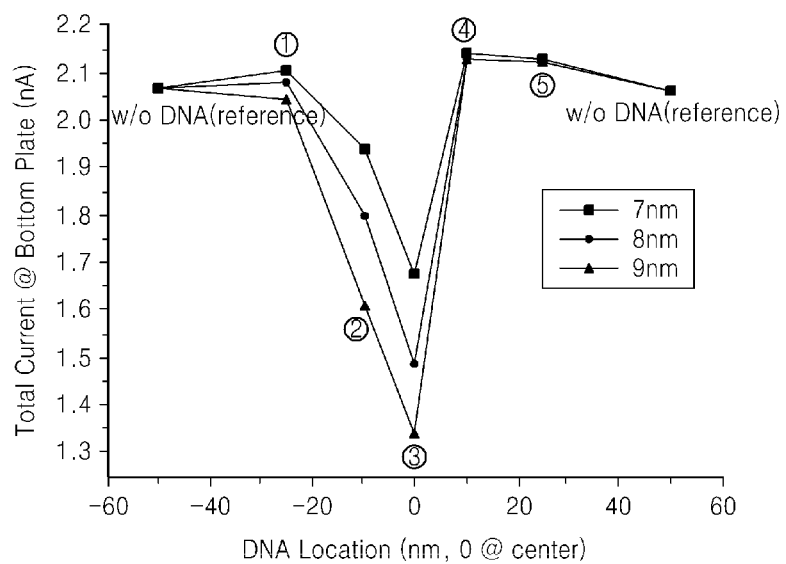
FIG. 5 is a graph showing characteristics whereby a current between source/drain electrodes is changed according to the size of a base and a position through which a base translocates when bases having different sizes translocate through a nanopore.

FIG. 5 is a graph showing changes in current between the first and second source/drain electrodes 62 and 64 as a nucleic acid translocates through a nanopore. The current changes according to the size of a base and the position in the nanopore. Referring to FIG. 5, as the size of a base is increased, the current is changed more when the base translocates through the nanopore 41b. Accordingly, the nanopore device according to the present embodiment may detect a change in voltage or current to accurately analyze a base sequence of DNA. In particular, as described above, the thickness of the gate electrode 30 and the diameter of the nanopore 41b may be restricted so as to reduce measurement noise, thereby increasing accuracy.

Figure 6:
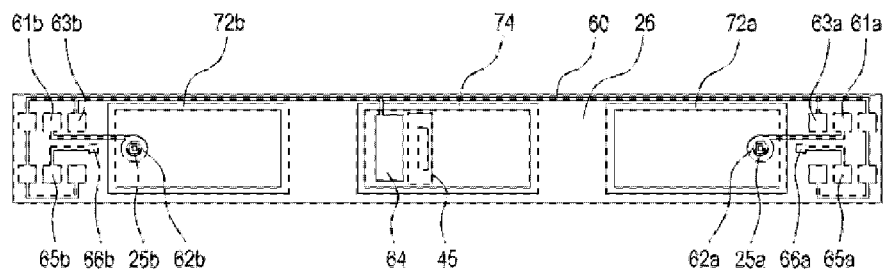
FIG. 6 is a plan view of a nanopore device array according to an embodiment of the present invention.

According to the present embodiment, since the first and second solution reservoirs 72 and 74 are horizontally formed on the upper surface of the cover unit 80, convenience of use is ensured. As described below, a plurality of first solution reservoirs are disposed around the second solution reservoir 74, and thus, a nanopore device array may be easily embodied. FIG. 6 is a plan view of a nanopore device array according to an embodiment of the present invention.

Referring to FIG. 6, in the nanopore device array according to the present embodiment, two or more first solution reservoirs, that is, first solution reservoirs 72a and 72b may share the micro channel 11 with each other and may be connected to each other around the second solution reservoir 74. Nanopores 41b may be respectively disposed to correspond to the first solution reservoirs 72a and 72b. In FIG. 6, for convenience of description, nanopore inlets 25a and 25b are shown to respectively correspond to the first solution reservoirs 72a and 72b. In addition, a first source/drain electrode 62a and 62b, gate contact plugs 66a and 66b, and contact units 61a, 61b, 63a, 63b, 65a, and 65b may be formed on the cover unit 80 to respectively correspond to the nanopore inlets 25a and 25b. The remaining portions of the nanopore device array shown in FIG. 6 are the same as in the nanopore device described with reference to FIGS. 1, 2A, and 2B, and thus, the details thereof will be omitted.

In this structure, when a negative voltage is applied to the first source/drain electrode 62a and 62b and a positive voltage is applied to the second source/drain electrode 64, target materials contained in the first solution reservoirs 72a and 72b may translocate through the nanopore 41b and then may be collected in the second solution reservoir 74 through the micro channel 11. According to the present embodiment, a large amount of samples may be simultaneously analyzed by using a plurality of solution containers, that is, the first solution containers 72a and 72b.

Hereinafter, a method of fabricating the nanopore device shown in FIG. 1 will be described with reference to FIGS. 7 through 22. Reference numerals that are not described with reference to FIG. 1 through 6 will be described with reference to FIGS. 7 through 22. In each of FIGS. 7 through 22, (a) is a plan view and (b) is a cross-sectional view taken along a line A-A'.

Figure 7:
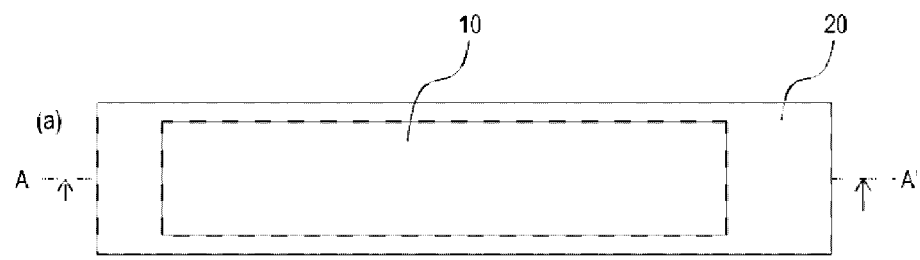
FIGS. 7 through 22 are diagrams for describing a method of fabricating the nanopore device of FIG. 1, according to an embodiment of the present invention.
Figure 7:
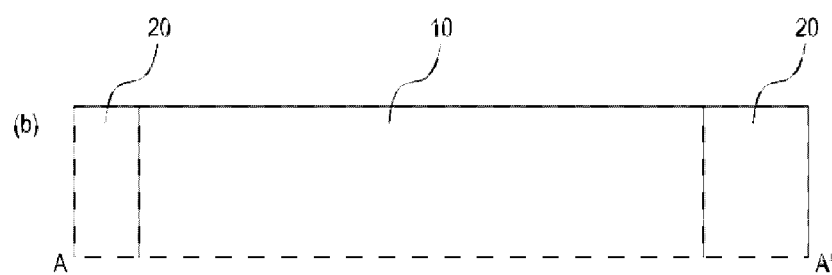

Referring to FIG. 7, an insulator lateral wall 20 is formed around an edge portion of a semiconductor substrate. For example, the insulator lateral wall 20 may be formed by forming a trench in the edge portion of the semiconductor substrate by using a general STI process and filling an insulating layer in the trench. For example, the insulator lateral wall 20 may comprise any suitable insulator material, such as $SiO_2$. Then, an active region 10 that will be processed in a subsequent process may remain on a central portion of the semiconductor substrate. In this case, the semiconductor substrate may be, for example, a bulk silicon substrate or a silicon-on-insulator (SOI) substrate.

Figure 8:
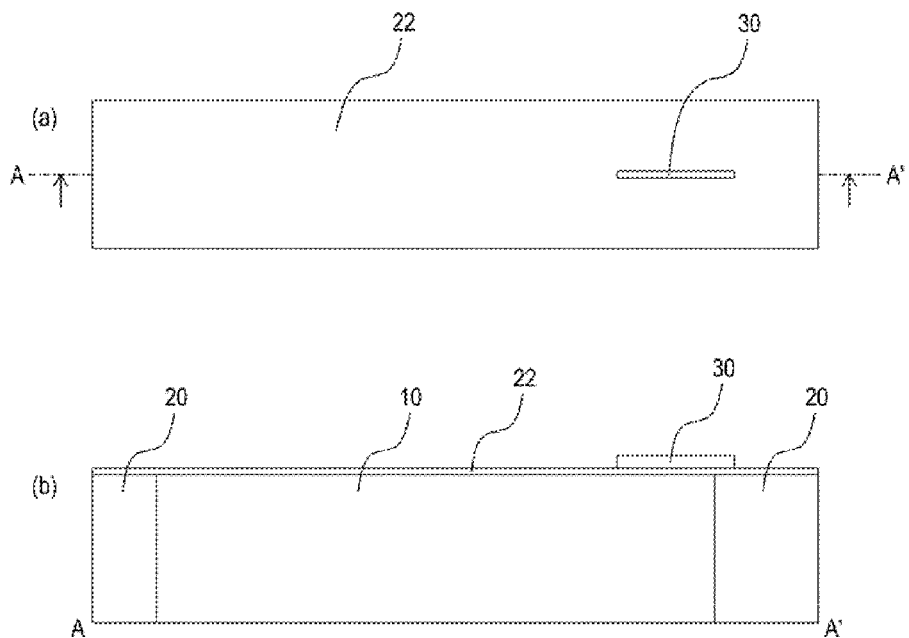

Then, as shown in FIG. 8, the first insulating layer 22 is formed on an entire upper surface of the semiconductor substrate, contacting the active central region of the semiconductor substrate and the insulator lateral wall region, and then the gate electrode 30 is partially formed on the first insulating layer 22. In this case, the gate electrode 30 may be formed over an interface between the active region 10 and the insulator lateral wall 20. In other words, the gate electrode is positioned on a region of the first insulating layer that overlaps the interface between the active region and the insulator lateral wall. The first insulating layer 22 may be formed of a silicon oxide, for example, $SiO_2$. The gate electrode 30 may be formed of metal or a silicon-based material (e.g., poly silicon) doped with impurities. When the nanopore device is used to analyze a base sequence of DNA, since an interval between bases is about 0.33 nm, a thickness of the gate electrode 30 may be about 0.3 nm to about 0.4 nm. According to the present embodiment, since the nanopore device is manufactured by using a general semiconductor process, the gate electrode 30 may be formed to have a small thickness. In addition, for example, the gate electrode 30 may be formed of a thin electrode material such as graphene.

Figure 9:
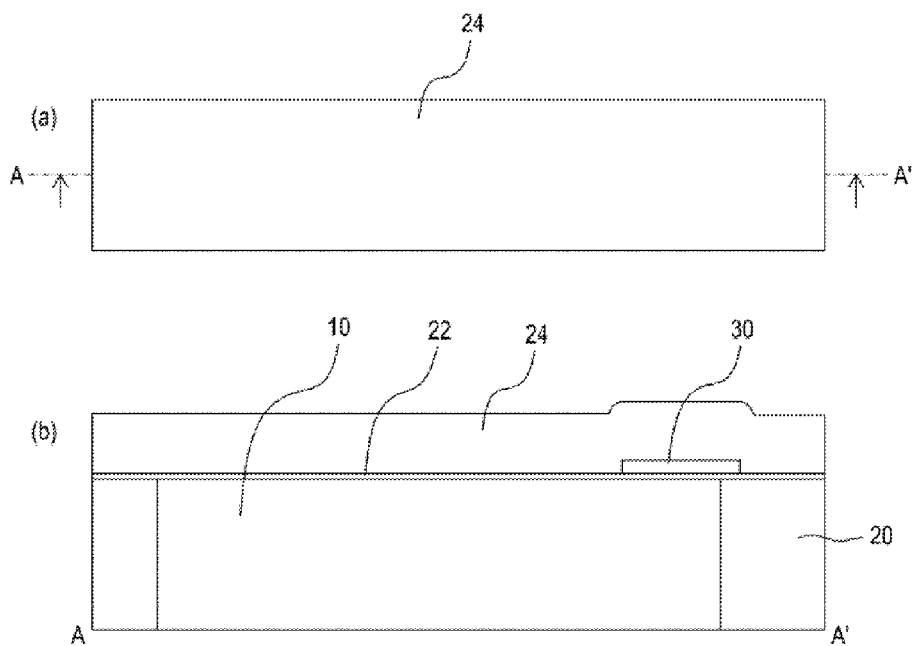
Figure 10:
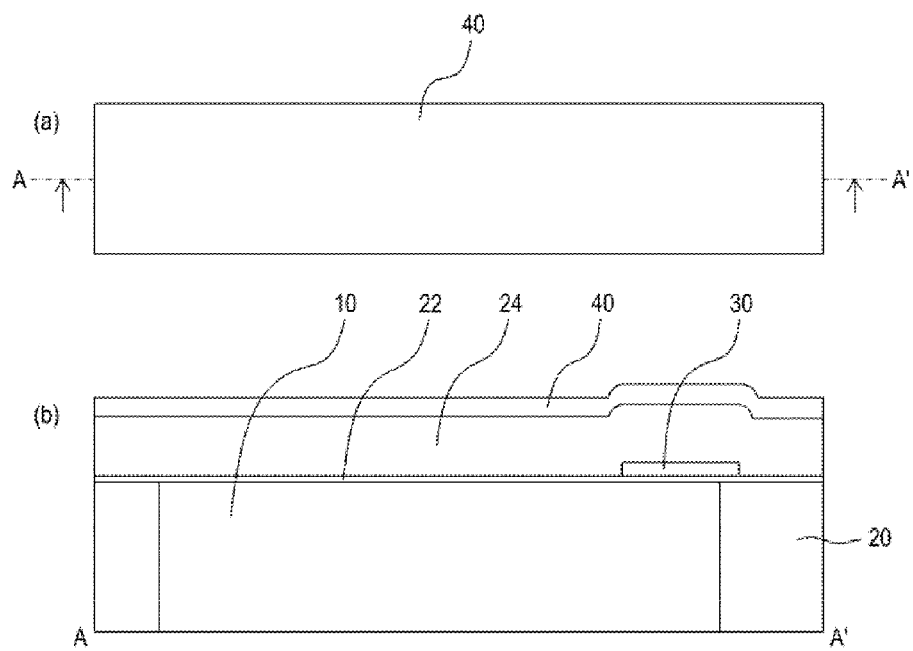

Then, referring to FIGS. 9 and 10, the second insulating layer 24 and the third insulating layer 40 are sequentially stacked on the first insulating layer 22 on which the gate electrode 30 is formed. The second insulating layer 24 may be formed as the same oxide layer as the first insulating layer 22. However, since the third insulating layer 40 serves as a mask in an etch process with respect to the first and second insulating layers 22 and 24 that will be described below, the third insulating layer 40 may be formed of an insulating material having a different etch rate from the first and second insulating layers 22 and 24. For example, the third insulating layer 40 may be formed of silicon nitride (SiNx) such as $Si_3N_4$.

Figure 11:
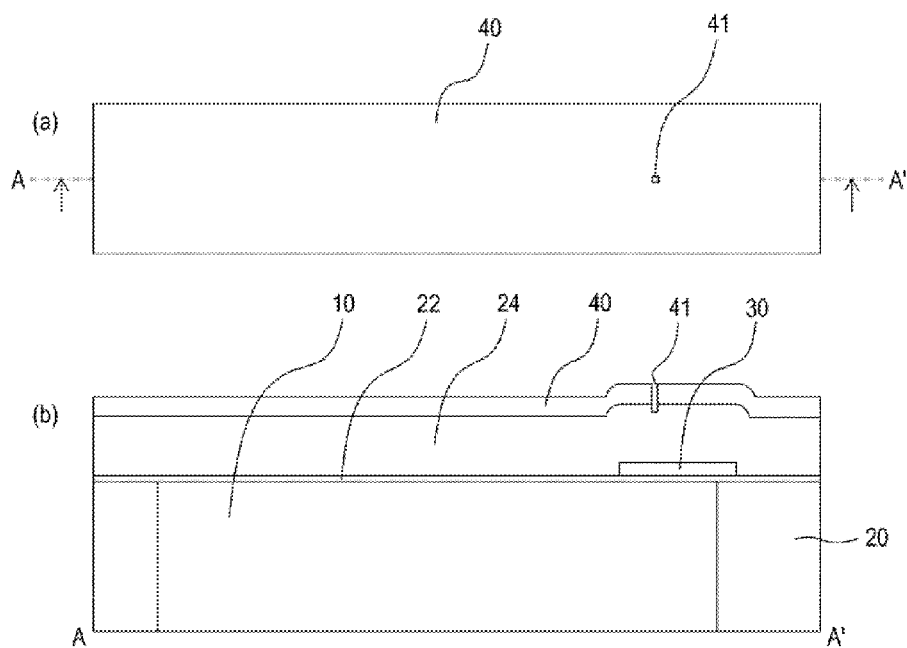

Then, as shown in FIG. 11, a second via hole 41 is formed through the third insulating layer 40. The second via hole 41 may be formed to face the active region 10 and the gate electrode 30. In other words, the second via hole 41 is positioned in a region of the third insulating layer that overlaps the gate electrode and the active central region of the semiconductor substrate. When the second via hole 41 is formed, the second insulating layer 24 may be partially etched.

Figure 12:
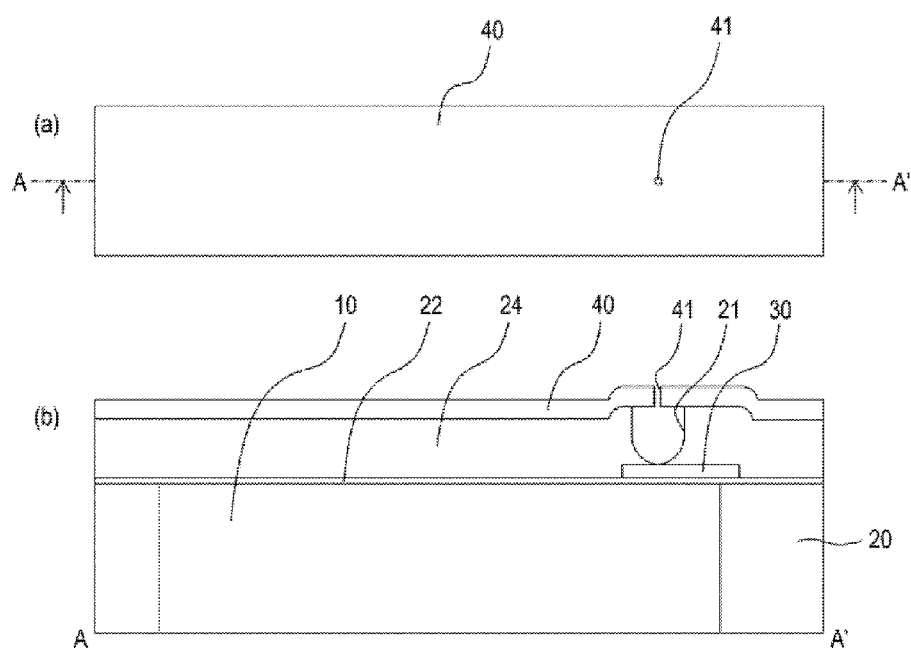
Figure 13:
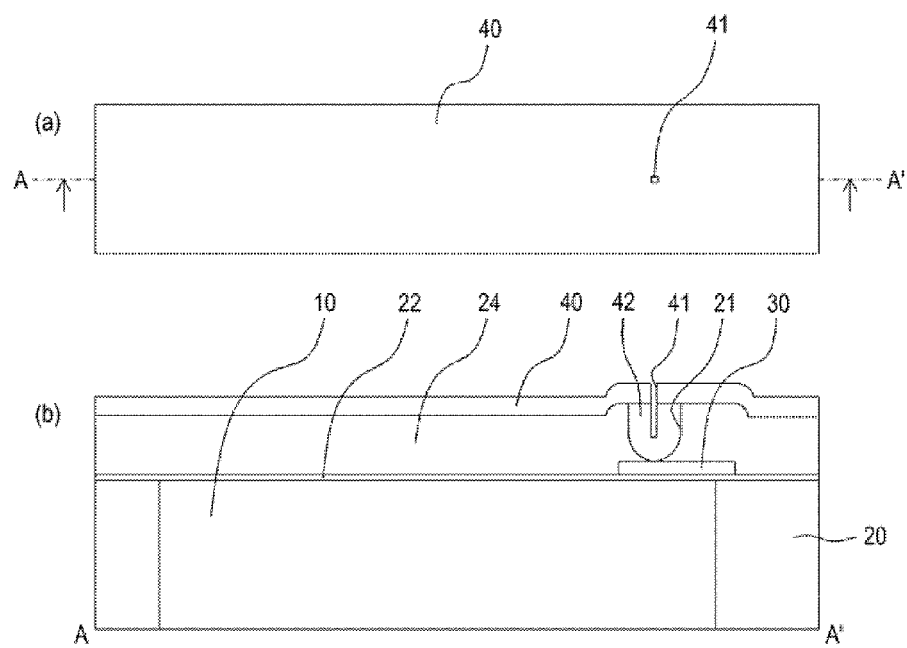

As shown in FIG. 12, an etchant is provided through the second via hole 41 so as to wet-etch the second insulating layer 24. Then, the gate electrode 30 may be exposed through a portion 21 that is removed by etching the second insulating layer 24. The wet etching is performed until the gate electrode 30 is at least partially exposed. When the gate electrode 30 is exposed, a spacer 42 is formed by filling the same material as the third insulating layer 40 in the portion 21 that is removed by etching the second insulating layer 24, as shown in FIG. 13.

Figure 14:
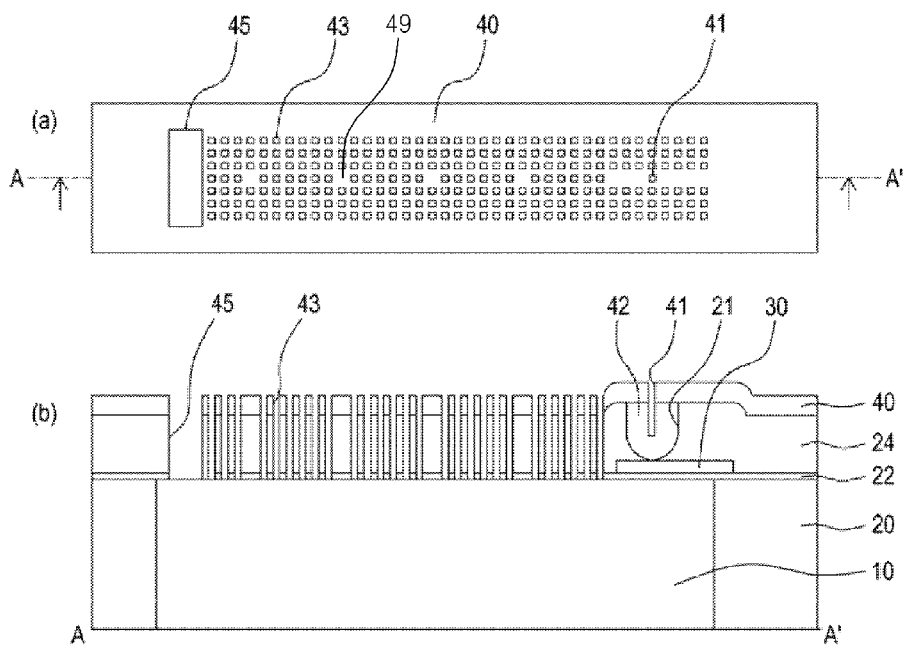

Then, referring to FIG. 14, a plurality of first via holes 43 and the opening 45 are formed through the first through third insulating layers 22, 24, and 40. In this case, the first via holes 43 and the opening 45 are formed in a region corresponding to the active region 10, except for a region corresponding to the gate electrode 30, so as to expose the active region 10. The first via holes 43 may be spaced apart from each other along columns and rows by a predetermined interval. In this case, at least one barrier or barriers 49 may be regularly or irregularly arranged between the first via holes 43 and may each have a horizontal cross-sectional area that is at least three times or more greater than the size of each of the first via holes 43. The barriers 49 may be unetched portions of the third insulating layer 40 while forming the first via holes 43 through the third insulating layer 40. The barriers 49 serve as a mask so that a portion of the active region 10 corresponding to the barriers 49 remains after a subsequent process of forming the micro channel 11 by etching the active region 10. The portion of the active region 10, which remains in the micro channel 11, may function as a column for supporting the cover unit 80. In FIG. 14, a ratio between the size of the first via holes 43 and the size of the barriers 49 is just an example. In reality, the size of the barriers 49 may be much greater than the size of the first via holes 43. The opening 45 may be formed on the active region 10 to be opposite to the gate electrode 30. For example, an opening area of the opening 45 may be at least two times or more greater than an opening area of the nanopore 41b that will be formed later.

Figure 15:
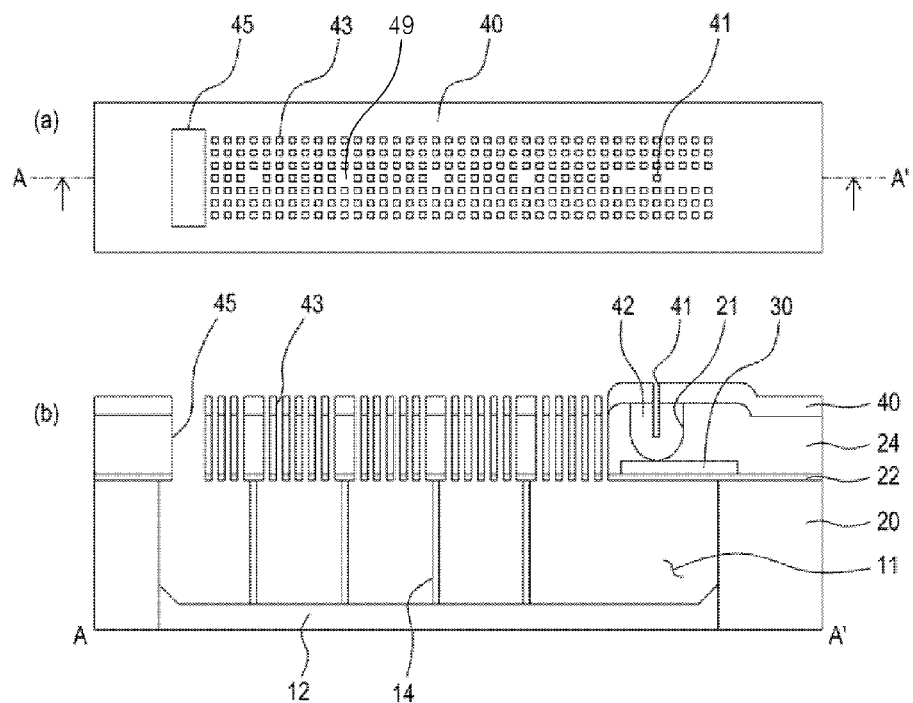

Then, referring to FIG. 15, an etchant may be provided through the first via holes 43 and the opening 45 to wet-etch the active region 10. Then, a portion of the active region 10, which is below the first insulating layer 22, may be etched and removed to form the micro channel 11 having a predetermined space below the first insulating layer 22. The wet etching is performed for a predetermined period of time according to the thickness of the active region 10 so that the bottom surface 12 may remain below the active region 10. In addition, the wet etching is performed in an under-cut manner so that the active region 10 may partially remain below the barriers 49 disposed between the first via holes 43 to form at least one column 14. The micro channel 11 may also be formed by isotropic dry etching instead of wet etching.

Figure 16:
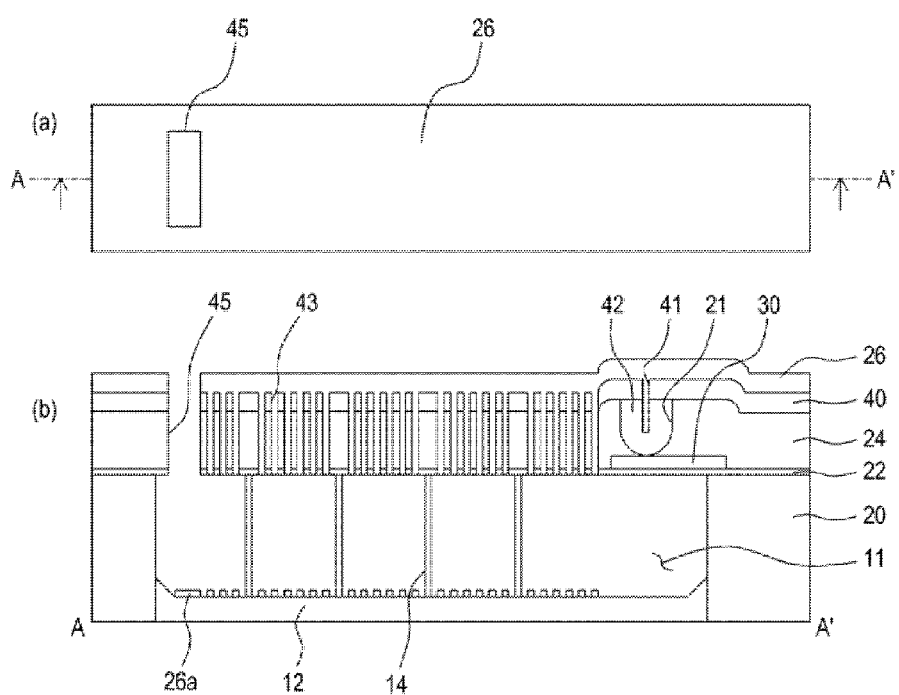

Then, as shown in FIG. 16, the fourth insulating layer 26 may be formed to a predetermined thickness on an entire upper surface of the third insulating layer 40. Then, the second via hole 41 and the first via holes 43 may be covered and/or filled (completely or partially) with the fourth insulating layer 26. In order to fill the second via hole 41 and the first via holes 43, the fourth insulating layer 26 may be formed by using, for example, a sputtering method. The fourth insulating layer 26 may be formed of the same oxide material as the first insulating layer 22. When the fourth insulating layer 26 is formed, a material 26a of the fourth insulating layer 26 may partially remain on the bottom surface 12.

Figure 17:
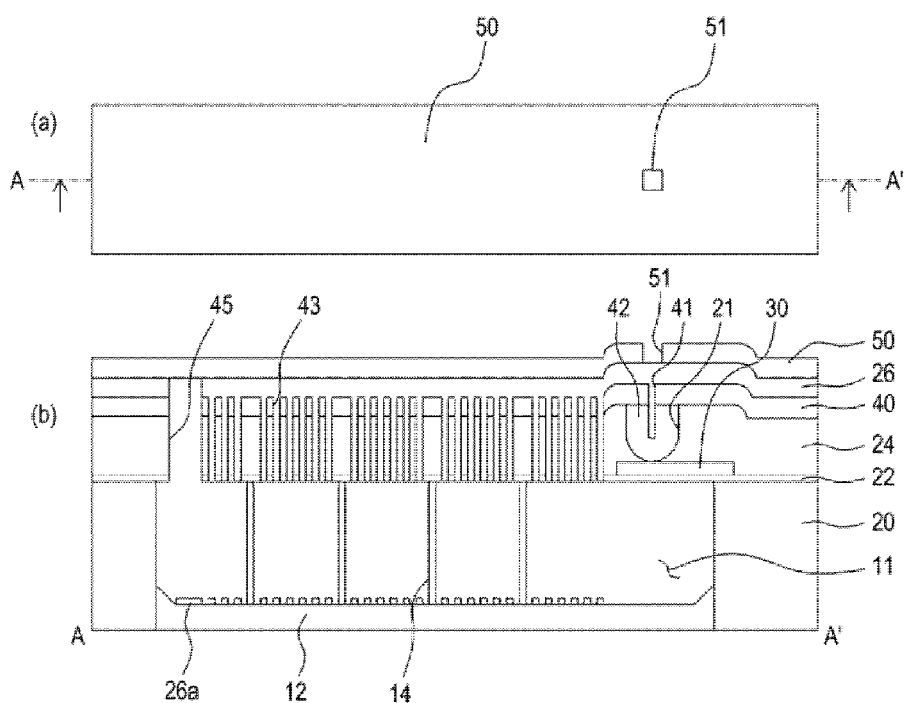
Figure 18:
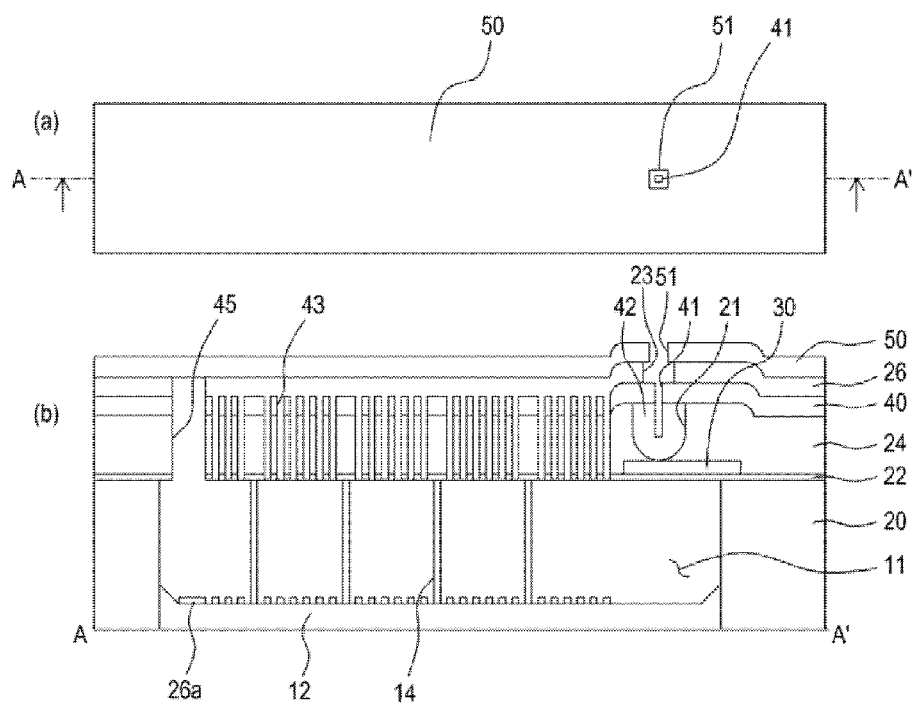

Then, referring to FIG. 17, a mask pattern 51 is formed by stacking a mask layer 50 on the fourth insulating layer 26 and etching the mask layer 50 so as to remove a portion of the mask layer 50 corresponding to the second via hole 41. Then, as shown in FIG. 18, the fourth insulating layer 26 may be etched through the mask pattern 51 so as to expose the second via hole 41. For example, the fourth insulating layer 26 may be wet-etched. Then, a portion of the fourth insulating layer 26 may be removed above the second via hole 41 to form a predetermined space 23.

Figure 19:
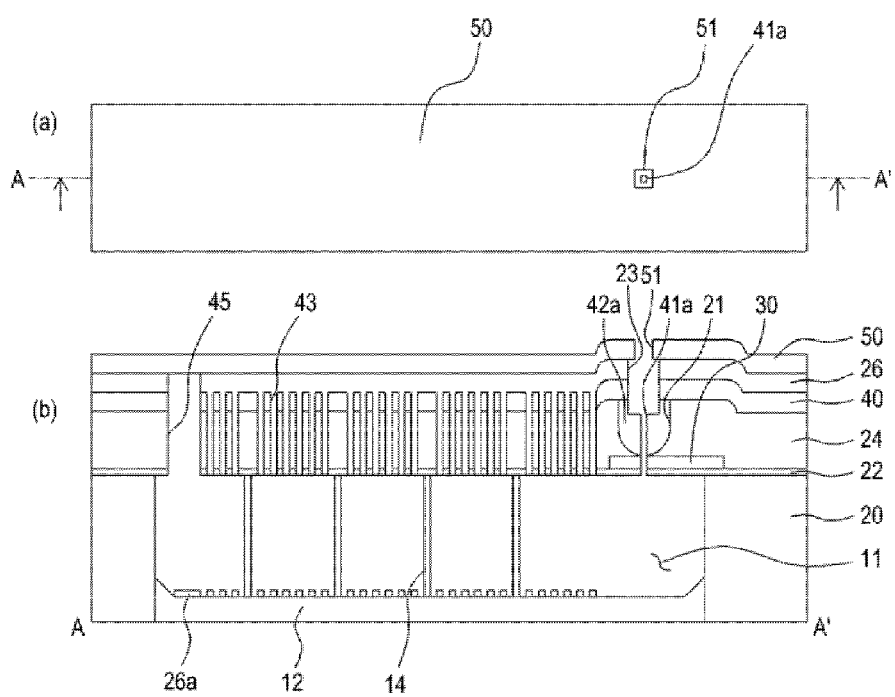
Figure 20:
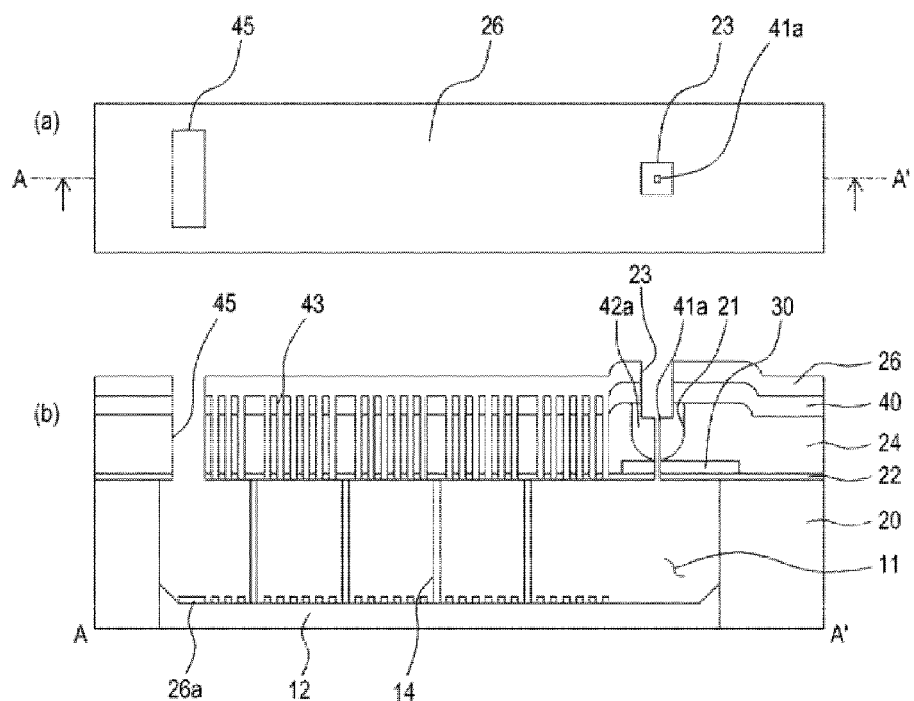

Then, as shown in FIG. 19, the spacer 42, the gate electrode 30, and the first insulating layer 22 may be sequentially etched through the mask pattern 51 and the second via hole 41 to form a nanopore 41a. In this case, the spacer 42, the gate electrode 30, and the first insulating layer 22 may be etched by anisotropic dry etching. After the nanopore 41a is formed, the mask layer 50 is removed, as shown in FIG. 20.

Figure 21:
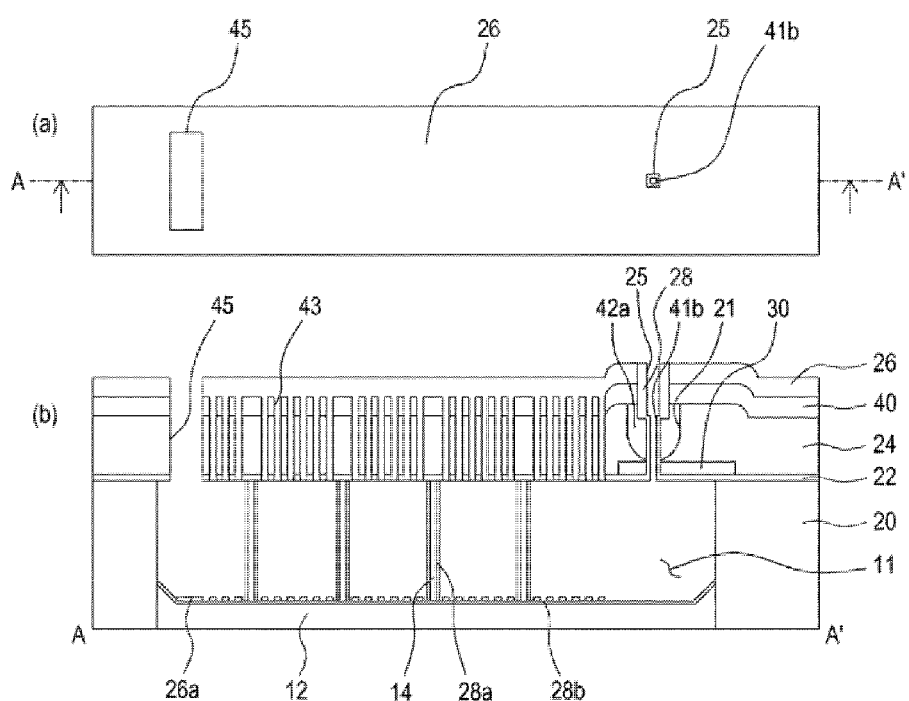

Then, as shown in FIG. 21, the gate insulating layer 28 is formed on an internal wall of the nanopore 41a. The gate insulating layer 28 may be formed to cover at least the exposed portion of the gate electrode 30. Thus, the nanopore device according to the present embodiment may operate as an IFET. In addition, by forming the gate insulating layer 28, a final nanopore 41b may have a reduced internal diameter. Since a diameter of a single-stranded DNA is about 1 nm, the final nanopore 41b may be formed to have a diameter of about 1 nm to about 1.5 nm. To this end, a process condition for forming the gate insulating layer 28 may be appropriately controlled. For example, the gate insulating layer 28 may be formed by using a thermal oxidation process. In this regard, the diameter of the final nanopore 41b may be controlled by controlling the duration of the processing period. When the gate insulating layer 28 is formed by using the thermal oxidation process, an oxidation layer may be formed in a portion of the micro channel 11, through which silicon is exposed. For example, an oxidation layer 28a may be formed on a surface of the bottom surface 12 and the oxidation layer 28a may also be formed on surfaces of the columns 14.

Figure 22:
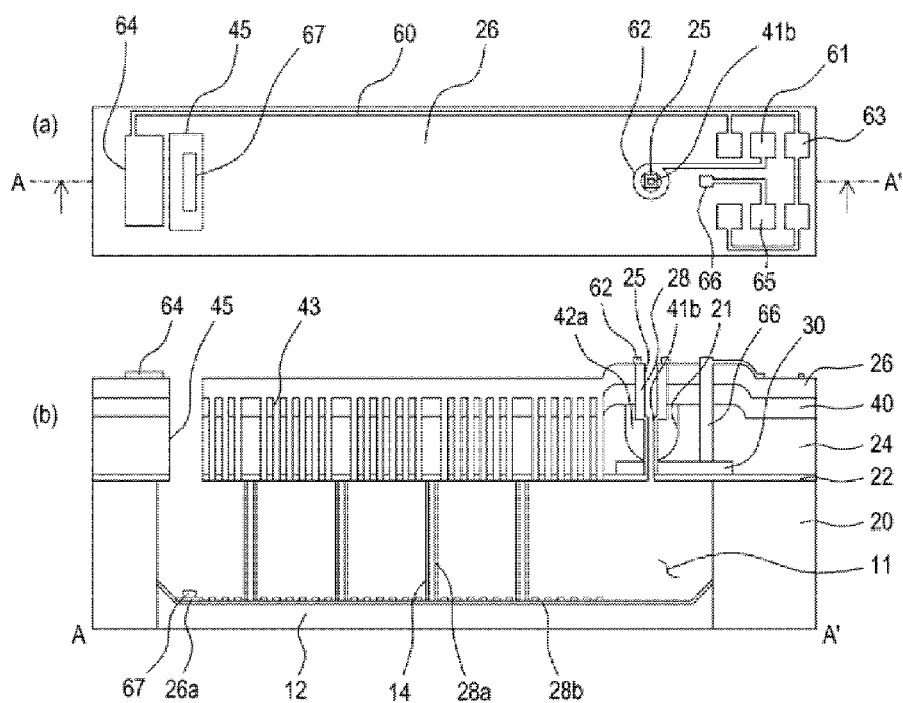

Lastly, referring to FIG. 22, the fourth insulating layer 26, the third insulating layer 40, and the second insulating layer 24 are sequentially etched so as to expose a portion of the gate electrode 30 to form a contact hole. Then, the first source/drain electrode 62, the second source/drain electrode 64, the gate contact plug 66, and wirings 60 may be formed on the fourth insulating layer 26. In this case, an electrode material 67 may also be partially deposited on the bottom surface 12 through the opening 45. Although not illustrated, signal amplifying circuits that are respectively connected to the gate contact plug 66, the first source/drain electrode 62, and the second source/drain electrode 64 so as to amplify measuring signals may be further formed on the fourth insulating layer 26.

As shown in FIGS. 1, 2A, and 2B, the first solution reservoir 72 and the second solution reservoir 74 may be further formed on the fourth insulating layer 26. The first solution reservoir 72 may be formed to surround the nanopore 41b and the first source/drain electrode 62. The second solution reservoir 74 may be formed to surround the opening 45 and the second source/drain electrode 64. As described above, the first and second solution reservoirs 72 and 74 may each be formed with a hydrophobic wall. For example, the first and second solution reservoirs 72 and 74 may be formed of a photosensitive layer or polydimethylsiloxane (PDMS) and then adhered onto the fourth insulating layer 26.

Since the above-described method of fabricating a nanopore device uses a semiconductor process, a diameter of the nanopore 41b and a thickness of the gate electrode 30 may be minimized. For example, the gate electrode 30 having a small thickness may be formed by using a metal deposition process or a growth process of polysilicon. The diameter of the nanopore 41b may be reduced by forming the gate insulating layer 28 by using a thermal oxidation process. Since the nanopore device is formed on a semiconductor substrate, a signal amplifying circuit may be formed to be integrated with the nanopore device. In addition, a typical semiconductor process is used, and thus the nanopore device may be easily manufactured. Since the nanopore device includes two solution reservoirs 72 and 74 that are horizontally disposed on the cover unit 80, the nanopore device may be easily manufactured and used. For example, since the first source/drain electrode 62, the second source/drain electrode 64, the gate contact plug 66, and the wirings 60 are disposed on the upper surface of the cover unit 80, a complex manufacturing process is not required and all manipulations may be performed on the upper surface of the cover unit 80 during use of the nanopore device. In addition, a nanopore device array may be formed using similar techniques.

As described above, according to the one or more of the above embodiments of the present invention, examples are explained and drawings are described in order to help in the understanding of a nanopore device and a method of fabricating the same. However, it should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:
1. A nanopore device comprising:
a channel unit comprising a micro channel defined by a bottom surface and an insulator lateral wall; and
a cover unit covering the micro channel,
wherein the cover unit comprises:
a nanopore extending through the cover unit and connected to the micro channel;
a first source/drain electrode disposed on an upper surface of the cover unit and adjacent to an inlet of the nanopore;
an opening extending through the cover unit and connected to the micro channel;
a second source/drain electrode disposed on the upper surface of the cover unit and adjacent to the opening; and
a gate electrode that surrounds the nanopore.
2. The nanopore device of claim 1, wherein the cover unit further comprises a gate insulating layer that covers the gate electrode on an internal wall of the nanopore.
3. The nanopore device of claim 1, further comprising:
a gate contact plug extending through the cover unit and electrically connected to the gate electrode; and
a contact unit disposed on the upper surface of the cover unit and electrically connected to the gate contact plug, the first source/drain electrode, and the second source/drain electrode through electrical wiring.
4. The nanopore device of claim 1, wherein thickness of the gate electrode is about 0.3 nm to about 0.4 nm, and
an internal diameter of the nanopore is about 1 nm to about 1.5 nm in an area where the gate electrode is disposed.
5. The nanopore device of claim 1, wherein the cover unit further comprises:
a first solution reservoir that protrudes from the upper surface of the cover unit and surrounds the nanopore and the first source/drain electrode; and
a second solution reservoir that protrudes from the upper surface of the cover unit and surrounds the opening and the second source/drain electrode.
6. The nanopore device of claim 5, wherein the first solution reservoir and the second solution reservoir are each comprise a hydrophobic wall.
7. The nanopore device of claim 5, wherein the cover unit comprises a plurality of first solution reservoirs.
8. The nanopore device of claim 7, wherein the cover unit comprises a plurality of nanopores and a plurality of first source/drain electrodes that are respectively disposed in the plurality of first solution reservoirs.
9. The nanopore device of claim 7, wherein the second solution reservoir is disposed between the plurality of first solution reservoirs.
10. The nanopore device of claim 1, wherein the bottom surface comprises a semiconductor material.
11. The nanopore device of claim 1, wherein the cover unit comprises a stack having at least one insulating layer.
12. The nanopore device of claim 1, wherein an opening area of the opening is greater than an opening area of the nanopore.
13. A method of analyzing a nucleic acid molecule comprising contacting the nanopore of the device of claim 1 with a sample comprising a nucleic acid, applying an electric current between the first and second source/drain electrodes, and detecting a change in the voltage between the first and second source/drain electrodes.
14. The method of claim 13, wherein the relative magnitude of a change in the voltage between the first and second source/drain electrodes indicates the relative size of a base of the nucleic acid passing through the nanopore.
15. A method of analyzing a nucleic acid molecule comprising contacting the nanopore of the device of claim 1 with a sample comprising a nucleic acid, applying an electric current between the first and second source/drain electrodes, and detecting a change in voltage at the gate electrode.

16. A nanopore device comprising:
a channel unit comprising a micro channel defined by a bottom surface and an insulator lateral wall; and
a cover unit covering the micro channel,
wherein the cover unit comprises:
a nanopore extending through the cover unit and connected to the micro channel;
a first source/drain electrode disposed on an upper surface of the cover unit and adjacent to an inlet of the nanopore;
an opening extending through the cover unit and connected to the micro channel;
a second source/drain electrode disposed on the upper surface of the cover unit and adjacent to the opening; and
at least one column connected between an upper surface of the bottom surface and a lower surface of the cover unit in the micro channel and supporting the cover unit.

17. A nanopore device comprising:
a channel unit comprising a micro channel defined by a bottom surface and an insulator lateral wall; and
a cover unit covering the micro channel,
wherein the cover unit comprises:
a nanopore extending through the cover unit and connected to the micro channel;
a first source/drain electrode disposed on an upper surface of the cover unit and adjacent to an inlet of the nanopore;
an opening extending through the cover unit and connected to the micro channel; and
a second source/drain electrode disposed on the upper surface of the cover unit and adjacent to the opening;
wherein the first source/drain electrode has a ring shape and surrounds the inlet of the nanopore.

* * * * *